US008211880B2

(12) United States Patent
Kabra et al.

(10) Patent No.: US 8,211,880 B2
(45) Date of Patent: Jul. 3, 2012

(54) LOW VISCOSITY, HIGHLY FLOCCULATED TRIAMCINOLONE ACETONIDE SUSPENSIONS FOR INTRAVITREAL INJECTION

(75) Inventors: Bhagwati P. Kabra, Euless, TX (US); Ruma Sarkar, Fort Worth, TX (US)

(73) Assignee: Alcon Research, Ltd., Fort Worth, TX (US)

(*) Notice: Subject to any disclaimer, the term of this patent is extended or adjusted under 35 U.S.C. 154(b) by 0 days.

(21) Appl. No.: 13/352,009

(22) Filed: Jan. 17, 2012

(65) Prior Publication Data

US 2012/0116216 A1 May 10, 2012

Related U.S. Application Data

(62) Division of application No. 12/401,168, filed on Mar. 10, 2009, now Pat. No. 8,128,960.

(60) Provisional application No. 61/035,459, filed on Mar. 11, 2008.

(51) Int. Cl.
*A61K 31/56* (2006.01)
(52) U.S. Cl. ......... 514/180; 514/169; 514/912; 514/913
(58) Field of Classification Search .................. 514/169, 514/180, 912, 913
See application file for complete search history.

(56) References Cited

U.S. PATENT DOCUMENTS

| | | | |
|---|---|---|---|
| 3,962,430 A | 6/1976 | O'Neill | |
| 4,370,325 A | 1/1983 | Packman | |
| 4,432,964 A | 2/1984 | Shell et al. | |
| 5,728,690 A | 3/1998 | Chen | |
| 5,770,589 A | 6/1998 | Billison et al. | |
| 6,395,294 B1 | 5/2002 | Peyman | |
| 2003/0129242 A1 | 7/2003 | Bosch et al. | |
| 2004/0186084 A1 | 9/2004 | Alam et al. | |
| 2005/0101582 A1 | 5/2005 | Lyons et al. | |
| 2005/0244469 A1 | 11/2005 | Whitcup et al. | |
| 2006/0141049 A1 | 6/2006 | Lyons et al. | |
| 2006/0154910 A1 | 7/2006 | Bingaman et al. | |
| 2007/0224278 A1 | 9/2007 | Lyons et al. | |
| 2007/0225727 A1 | 9/2007 | Matsuhisa et al. | |
| 2008/0008762 A1 | 1/2008 | Robinson et al. | |
| 2008/0009471 A1 | 1/2008 | Higuchi et al. | |
| 2008/0044476 A1 | 2/2008 | Lyons et al. | |

FOREIGN PATENT DOCUMENTS

| | | |
|---|---|---|
| EP | 1782795 A1 | 9/2007 |
| EP | 1867334 A1 | 12/2008 |
| WO | WO0002564 A1 | 1/2000 |
| WO | WO0128563 A1 | 4/2001 |
| WO | WO0149226 A1 | 7/2001 |
| WO | WO2005032510 A1 | 4/2005 |
| WO | WO2005046641 A2 | 5/2005 |
| WO | WO2005072701 A1 | 8/2005 |
| WO | WO2006055954 A2 | 5/2006 |

OTHER PUBLICATIONS

Bitter, et al., Preservative-free Triamcinolone Acetonide Suspension Developed for Intravitreal Injection, Journal of Ocular Pharmacology and Therapeutics, 2008, pp. 62-69, vol. 24, No. 1.
Nov. 2007 Triesence Advertisement, VIT674, Alcon, Alcon Laboratories, Inc., Fort Worth, Texas 76134.
Triesence Package Insert, Nov. 2007, Triesence™ (triamcinolone acetonide injectable suspension) 40 mg/mL., Initial U.S. Approval: 1957.
Morrison, et al., "Intravitreal Toxicity of the Kenalog Vehicle (Benzyl Alcohol) in Rabbits," Retina, 2006, pp. 339-344, vol. 26.
Furrer, et al., "Ocular Tolerance of Preservatives and Alternatives," European Journal of Pharmaceutics and Biopharmaceutics, vol. 53, Issue 3, May 2002, pp. 263-280.
Rowe, Handbook of Pharmaceutical Excipients-Carboxymethylcellulose Sodium, Pharmaceutical Press, 2003, 97-100, 5 pages.
www.AMD.org. What is AMD?, printed from http://www.amd.org/what-is-amd.html on Aug. 3, 2010, 2 pages.
www.allnurses.com, Help Hypotonic, Isotonic, & Hypertonic Solutions, Nov. 27, 2006, http://allnurses.com/nursing-student-assistance/help-hypotonic-isotonic-192228.html, 4 pages.
Patel, Rajesh-M., Parenteral Suspension: An Overview, International Journal of Current Pharmaceutical Research, Jan. 30, 2010, pp. 4-13, vol. 2, Issue 3.

*Primary Examiner* — Sreeni Padmanabhan
*Assistant Examiner* — Gigi Huang
(74) *Attorney, Agent, or Firm* — Patrick M. Ryan

(57) ABSTRACT

Triamcinolone acetonide suspension compositions are disclosed. The suspension compositions have a relatively low viscosity and are easy to extrude through a 27- or 30-guage needle but are highly flocculated and easily redispersed. The compositions are particularly suitable for intravitreal injection.

2 Claims, No Drawings

LOW VISCOSITY, HIGHLY FLOCCULATED TRIAMCINOLONE ACETONIDE SUSPENSIONS FOR INTRAVITREAL INJECTION

This application is a divisional application of Ser. No. 12/401,168, filed Mar. 10, 2009, which claims priority from U.S. Provisional Application Ser. No. 61/035,459, filed Mar. 11, 2008.

FIELD OF THE INVENTION

The present invention relates to injectable formulations used for treating diseases or conditions of the eye. More particularly, the present invention relates to suspension formulations that have a low viscosity and are highly (i.e. loosely) flocculated. The suspension formulations comprise the steroid triamcinolone or other poorly soluble drug compound.

BACKGROUND OF THE INVENTION

Injectable compositions containing triamcinolone acetonide have been available for many years. Commercial products include Kenalog®-10 Injection (triamcinolone acetonide injectable suspension, USP) and Kenalog®-40 Injection (triamcinolone acetonide injectable suspension, USP), which are marketed by Bristol-Myers Squibb Co. These products contain 10 mg/ml or 40 mg/ml of triamcinolone acetonide, respectively. According to its package insert, Kenalog-40 Injection is approved for certain intramuscular and intra-articular uses. Where oral therapy is not feasible or is temporarily undesirable in the judgment of the physician, Kenalog-40 Injection is indicated for intramuscular use in certain cases for endocrine disorders, rheumatic disorders, collagen diseases, dermatologic diseases, allergic states, ophthalmic diseases, gastrointestinal diseases, respiratory diseases, hematologic disorders, neoplastic diseases, and edematous state. The specific approved ophthalmic indication is "[s]evere chronic allergic and inflammatory processes involving the eye, such as: herpes zoster ophthalmicus; iritis; iridocyclitis; chorioretinitis; diffuse posterior uveitis and choroiditis; optic neuritis; sympathetic ophthalmia; and anterior segment inflammation. Kenalog-40 Injection is indicated for intra-articular or intrabursal administration, and for injection into tendon sheaths, as adjunctive therapy for short-term administration (to tide the patient over an acute episode or exacerbation) in the following conditions: synovitis of osteoarthritis; rheumatoid arthritis; acute and subacute bursitis; acute gouty arthritis; epicondylitis; acute nonspecific tenosynovitis; and posttraumatic osteoarthritis.

Recently, the use of Kenalog®-40 Injection to treat diabetic macular edema, has been growing more common. In this use, the product is injected into the vitreous of patients suffering from diabetic macular edema. In some cases, the product is processed by the physician or pharmacy in an attempt to remove the preservative that is present in the Kenalog-40 Injection formulation supplied by Bristol-Myers Squib Co. (i.e., benzyl alcohol) because the preservative may be irritating to the vitreous and tissues in the posterior segment of the eye. Additionally, the commercially available product must be used immediately after it is shaken to avoid settling; the package insert reads as follows: "After withdrawal [from the shaken product vial], inject without delay to prevent settling in the syringe."

What is needed is an improved triamcinolone acetonide suspension composition that is suitable for injection into the eye, does not settle rapidly, and can be easily injected through a small needle that offers the potential for a self-sealing puncture wound (e.g., 27-gauge or 30-gauge).

SUMMARY OF THE INVENTION

The present invention provides improved triamcinolone acetonide suspension compositions that are particularly suited for injection into the eye. The improved aqueous suspension compositions have excellent settling characteristics, are easily resuspended with gentle-shaking, are preservative-free, and are capable of being smoothly and easily injected through 30-gauge needles. In addition, the suspension compositions of the present invention can be terminally sterilized by autoclaving. The suspension compositions are also suitable for poorly soluble drugs other than triamcinolone.

Among other factors, the present invention is based on the finding that a suspension composition of triamcinolone acetonide that has improved settling characteristics relative to the currently available Kenalog-40 Injection triamcinolone acetonide composition can be obtained. The present invention is also based on the finding that a triamcinolone acetonide suspension composition containing a relatively low amount of surfactant has superior flocculation properties, relative to the currently available Kenalog-40 Injection composition, while still being both easily processed during manufacturing, transfer and filling operations, and easily extruded through a 27-gauge to 30-gauge needle.

DETAILED DESCRIPTION OF THE INVENTION

Unless indicated otherwise, all ingredient amounts are expressed on a weight/volume percent basis.

In a preferred embodiment, the aqueous suspension compositions of the present invention consist essentially of triamcinolone acetonide, carboxymethylcellulose, polysorbate 80, a pharmaceutically-acceptable tonicity-adjusting chloride salt, a buffering agent and water for injection.

Triamcinolone acetonide is a steroid that can be made by known methods and is commercially available in micronized forms. The triamcinolone acetonide should be sized so that mean volume diameter is 3-10 μm. Sizing techniques, such as ball-milling, are known and can be used to attain these particle size and distribution requirements. The suspension compositions of the present invention contain from 35-45 mg/ml (3.5-4.5%) of triamcinolone acetonide, preferably 40 mg/ml (4.0%) of triamcinolone acetonide.

In addition to triamcinolone acetonide, the suspension compositions of the present invention contain 0.45-0.55% sodium carboxymethylcellulose ("CMC"). Preferably, the compositions contain 0.5% CMC. CMC is commercially available from a variety of sources in different grades. For example, low (7LF PH), medium (7MF PH) and high (7HF PH) viscosity grades of CMC are available from Hercules Inc. The CMC ingredient included in the compositions of the present invention is preferably a low viscosity grade, such that the viscosity of a 2% solution of the CMC in water at 25° C. is 25-50 cps. (as measured using a Brookfield LVT viscometer with a CP-42 spindle at 60 rpm).

The compositions of the present invention have a viscosity of 2-12 cps, preferably 2-9 cps, and most preferably 2-8 cps. They settle slowly and resuspend readily. This relatively low viscosity ensures that the product is easily processed during manufacturing, transfer and filling operations, and is easily extruded through 27-gauge or 30-gauge needles.

Generally, pharmaceutical suspension compositions contain a surfactant to wet and disperse drug particles, and the amount of surfactant used is generally greater than the amount needed to fully wet the individual particles because such an excess helps make the particles easy to disperse. However, it can be extremely difficult to achieve a high degree of flocculation.

The amount of polysorbate 80 used in Kenalog-40 is 0.04%. However, it was found that if the surfactant concentration is significantly lower, e.g., 0.015%, the particles form loose floccules, thereby resulting in a high degree of flocculation. The low viscosity and high degree of flocculation of the compositions of the present invention ensures that they redisperse or resuspend easily upon gentle shaking. The compositions of the present invention therefore contain a reduced concentration of surfactant, relative to Kenalog-40. More specifically, the compositions of the present invention contain 0.002-0.02% polysorbate 80. Preferably, the compositions contain 0.01-0.02% polysorbate 80, and most preferably the compositions contain 0.015% polysorbate 80.

As used herein, "Degree of Flocculation" means the ratio of final sediment volume (i.e., as a percentage of the total volume) to particle concentration. For example, a suspension with a 4% particle (drug) concentration and a final sediment volume of 8% would have a Degree of Flocculation of 2. Similarly, a suspension composition with a 4% particle concentration and a final sediment volume of 20% would have a Degree of Flocculation of 5, and the same composition with a final sediment volume of 40% would have a Degree of Flocculation of 10.

The final sediment volume is the sediment volume (i.e., percentage of total volume) after prolonged room-temperature storage and does not significantly change with additional storage time. The final sediment volume can be reached quickly for low viscosity suspensions, e.g. in several hours to a few days, but it can take days or weeks to reach final sediment volume for medium to high viscosity systems.

Sediment volume can be determined as follows: place 10 mL of the suspension composition in a 10 mL graduated cylinder and record the sediment volume as a function of time. For example, if the sediment is up to 1 mL mark on the graduated cylinder, it represents a sediment volume of 10%. If this does not change significantly with additional storage time, then it is used as final sediment volume.

The compositions of the present invention have a Degree of Flocculation greater than 5, preferably greater than 6, and most preferably greater than 7.

The compositions of the present invention also comprise one or more pharmaceutically acceptable chloride salts as tonicity-adjusting agents. The most preferred chloride salt is sodium chloride. Preferably, the compositions comprise more than one chloride salt. In a most preferred embodiment, the compositions comprise sodium chloride, potassium chloride, calcium chloride, and magnesium chloride. The tonicity-adjusting agents are present in a total amount sufficient to provide the compositions of the present invention with an osmolality of 250-350 mOsm. In one embodiment, the compositions comprise 0.4-0.6% sodium chloride, 0.05-0.1% potassium chloride, 0.04-0.06% calcium chloride, and 0.01-0.04% magnesium chloride.

If necessary, the suspension compositions of the present invention also contain a pH-adjusting agent, such as NaOH or HCl to adjust the pH of the compositions to pH 6-7.5. The suspension compositions contain a pharmaceutically acceptable buffering agent to maintain the pH of the compositions within the range of 6-7.5, Suitable buffering agents include sodium acetate and sodium citrate. Preferably, the compositions contain a combination of sodium acetate and sodium citrate.

The suspension compositions of the present invention are preferably packaged in unit dose containers, such as glass or plastic vials. The suspension compositions can also be packaged in pre-filled syringes or cartridges.

As used herein, injection "into the posterior segment of the eye" includes, but is not limited to, injection into the vitreous body, injection into or beneath the sclera, and injection external to the vitreous and beneath the Tenon's capsule.

In one embodiment, the present invention relates to a method of treating macular edema including but not limited to diabetic macular edema, or retinal vein occlusion, including central and branch retinal vein occlusions, comprising injecting into the posterior segment of the eye the suspension composition described above. In another embodiment, the present invention relates to a method of treating post-surgical inflammation comprising injecting into the anterior segment of the eye the suspension composition described above. In still another embodiment, the present invention relates to a method of treating an ophthalmic disease or condition in the posterior segment of the eye, including but not limited to macular degeneration, comprising injecting into the posterior segment of the eye the suspension composition described above. For these embodiments in which a disease or condition of the eye is treated, the compositions of the present invention are preferably injected (e.g., into the vitreous or other locations in the posterior segment of the eye, or into the anterior chamber) so as to deliver an initial dose of 4 mg of triamcinolone acetonide (e.g., 100 microliters of 40 mg/mL suspension composition), with subsequent dosage as needed over the course of treatment.

In yet another embodiment, the present invention relates to a method of enhancing visualization of the vitreous during vitrectomy procedures. In this embodiment, the composition of the present invention is administered intravitreally so as to deliver 1 to 4 mg of triamcinolone acetonide (e.g., 25-100 microliters of 40 mg/mL suspension composition).

In another embodiment, the present invention relates to suspension compositions of poorly soluble drugs other than triamcinolone. As used herein, a "poorly soluble drug" is a drug that has a solubility at 22° C. of less than 1 mg/mL at pH 7.5 in phosphate buffered saline. The suspension compositions consist essentially of the poorly soluble drug compound, carboxymethylcellulose, polysorbate 80 or tyloxapol, a pharmaceutically-acceptable tonicity-adjusting chloride salt, optionally a buffering agent, optionally a pH-adjusting agent, and water for injection. The suspension compositions have a pH from 6-7.9, a viscosity of 2-12 cps, and a Degree of Flocculation greater than 5. Preferably, the suspension compositions consist essentially of:

a) 0.5 to 8.0% (w/v) of a poorly soluble drug, wherein the drug has a mean volume diameter of 3-10 μm;
b) 0.45-0.55% (w/v) sodium carboxymethylcellulose;
c) 0.002-0.02% (w/v) polysorbate 80 or tyloxapol;
d) one or more pharmaceutically acceptable chloride salts as tonicity-adjusting agents;
e) water for injection;
f) optionally a buffering agent; and
g) optionally a pH-adjusting agent to adjust the pH to 6-7.9.

The preferred concentration of polysorbate 80 or tyloxapol is 0.002-0.01% for compositions with a poorly soluble drug compound concentration ranging from 0.5-2%. The preferred concentration of polysorbate BO or tyloxapol is 0.01-0.02% for compositions with poorly soluble drug compound concentration ranging from 2-8%.

In one embodiment, poorly soluble drugs may be drugs for treating macular edema, retinal vein occlusion, geographic atrophy, dry age related macular degeneration, or wet age related macular degeneration. One example of such a poorly soluble drug is tandospirone.

The present invention also relates to a method of treating an ophthalmic disorder comprising administering by intravitreal injection a suspension composition consisting essentially of:
- a) 0.5 to 8.0% (w/v) of a poorly soluble drug, wherein the drug has a mean volume diameter of 3-10 µm;
- b) 0.45-0.55% (w/v) sodium carboxymethylcellulose;
- c) 0.002-0.02% (w/v) polysorbate 80 or tyloxapol;
- d) one or more pharmaceutically acceptable chloride salts as tonicity-adjusting agents;
- e) water for injection;
- f) optionally a buffering agent; and
- g) optionally a pH-adjusting agent to adjust the pH to 6-7.9.

Certain embodiments of the invention are illustrated in the following examples.

Example 1

The composition of Kenalog®-40 is shown in Table 1.1 below. It contains 4% triamcinolone acetonide and 0.04% polysorbate 80. The viscosity of this suspension is about 14 cps.

The particle size data for several lots was measured by laser light diffraction (Microtrac® S3000) and is shown in Table 1.2. The median particle size of the various lots of Kenalog-40 ranged from 13 to 22 µm.

The force required to extrude the Kenalog®-40 suspension through a one-half inch 30 gauge needle attached to a 1 mL tuberculin syringe is provided in Table 1.3. The results show that Kenlaog-40 suspension plugged the 30 gauge needle. The force required was quite variable and high. The plugging of the needle is due to the large particle size of this suspension.

The Kenalog®-40 suspension composition was determined to have a final sediment volume of about 14% and therefore has a Degree of Flocculation of 3.5. Thus, this suspension is only lightly flocculated, relative to the suspension compositions of the present invention.

TABLE 1.1

KENALOG-40 Composition

| Component | KENALOG-40 W/V % |
| --- | --- |
| Triamcinolone Acetonide | 4 |
| Carboxymethylcellulose Sodium | 0.75 |
| Polysorbate 80 | 0.04 |
| Benzyl Alcohol | 0.99 |
| Sodium Chloride | 0.75 |
| Sodium Hydroxide and/or Hydrochloric Acid | 5.0 to 7.5 |
| Water for Injection | qs to 100% |

TABLE 1.2

Particle Size Data for Six Lots of KENALOG-40, measured using Microtrac

| Manufacturer Lot Number (Expiration Date) | Particle Size (µm) × $_{10}$ (by Microtrac) | Particle Size (µm) × $_{50}$ (by Microtrac) | Particle Size (µm) × $_{90}$ (by Microtrac) |
| --- | --- | --- | --- |
| 5L01206 (October 2007) | 5.0 | 20.2 | 50.0 |
| 6B19016 (February 2008) | 3.5 | 13.6 | 38.6 |
| 6D16625 (April 2008) | 4.3 | 21.1 | 57.4 |
| 6F11285 (April 2008) | 3.4 | 13.6 | 40.9 |
| 6F15845 (April 2008) | 5.6 | 21.7 | 54.0 |
| 6D18800 (April 2008) | 4.2 | 15.7 | 41.6 |

TABLE 1.3

Extrusion Force Data For Kenalog-40 (1 mL Tuberculin Syringe with 30 GA × 1/2" needle)

| Formulation Description | Average Load lbs force (Standard Deviation) | Maximum Load lbs force |
| --- | --- | --- |
| Kenalog 40 mg/mL. lot 6F11285 Exp April 2008 | 5.33 (4.457) | 10.2 (Plugged in 4 out of 10 samples) |

Example 2

Triamcinolone acetonide suspensions with different concentrations of polysorbate 80 but without CMC were prepared as shown in Table 2.1. The mean volume particle size of the triamcinolone acetonide substance used in these compositions was 5-6 µm (measured using a Microtrae S3000 instrument).

A settling study was carried out on these formulations by placing 10 mL samples of each of them in separate 10 mL graduated cylinders and recording sediment volume as a function of time. Kenalog®-40 was studied as a control. The results are provided in Table 2.2. These results show that 4% triamcinolone formulations with polysorbate 80 concentrations less than 0.02% have high final sediment volumes. For these compositions, the sediment volume stabilized within a day and did not change for 7 days. The Degree of Flocculation for these samples ranged from 9.5 to 13.5, indicating that the compositions are highly flocculated. However, the formulations with a polysorbate 80 concentration of 0.02% and higher formed a compact sediment layer at the bottom of the graduated cylinder. The sediment volume in those cases was less than 10% and the Degree of Flocculation was around 2. Thus, formulations with a polysorbate 80 concentration 0.02% are not highly flocculated.

TABLE 2.1

Composition of Triamcinolone Acetonide Suspension without Viscosity Agents Used in the Settling Study

| Composition | A | B | C | D | E | F |
|---|---|---|---|---|---|---|
| Triamcinolone Acetonide | 4% | 4% | 4% | 4% | 4% | 4% |
| Polysorbate 80 | 0.002% | 0.005% | 0.01% | 0.015% | 0.02% | 0.025% |
| Sodium Chloride | 0.64% | 0.64% | 0.64% | 0.64% | 0.64% | 0.64% |
| Potassium Chloride | 0.075% | 0.075% | 0.075% | 0.075% | 0.075% | 0.075% |
| Calcium Chloride (Dihydrate) | 0.048% | 0.048% | 0.048% | 0.048% | 0.048% | 0.048% |
| Magnesium Chloride (Hexahydrate) | 0.03% | 0.03% | 0.03% | 0.03% | 0.03% | 0.03% |
| Sodium Acetate (Trihydrate) | 0.39% | 0.39% | 0.39% | 0.39% | 0.39% | 0.39% |
| Sodium Citrate (Dihydrate) | 0.17% | 0.17% | 0.17% | 0.17% | 0.17% | 0.17% |
| Sodium Hydroxide and/or Hydrochloric Acid | Adjust pH to 6.8 | Adjust pH to 6.8 | Adjust pH to 6.8 | Adjust pH to 6.8 | Adjust pH to 6.8 | Adjust pH to 6.8 |
| Water for Injection | qs to 100% | qs to 100% | qs to 100% | qs to 100% | qs to 100% | qs to 100% |

TABLE 2.2

Settling Study of Kenalog-40 and Triamcinolone Acetonide Suspension without CMC at different polysorbate 80 concentrations Time Point — Settling Phase in each 10 mL Volumetric Cylinder (Sedimentation Volume %)

| Composition | Kenalog-40 | A | B | C | D | E | F |
|---|---|---|---|---|---|---|---|
| Polysorbate 80 | 0.04% | 0.002% | 0.005% | 0.01% | 0.015% | 0.02% | 0.025% |
| Initial (0 mins) | Homogenous: 10 mL | Homogenous: 10 mL | Homogenous: 10 mL | Homogenous: 10 mL | Homogenous: 10 mL | Homogenous: 10 mL | Homogenous: 10 mL |
| 1 Hour | Sediment: 7.4 mL (74%) | Sediment: 5.2 mL (52%) | Sediment: 5.4 mL (54%) | Sediment: 5.2 mL (52%) | Sediment: 3.8 mL (38%) | Sediment 7.4 mL (74%) | Sediment: 7.2 mL (72%) |
| 2 Hours | Sediment: 5.0 mL (50%) | Sediment: 5.2 mL (52%) | Sediment: 5.4 mL (54%) | Sediment: 5.2 mL (52%) | Sediment: 3.8 mL (38%) | Sediment: 4.8 mL (48%) | Sediment: 4.2 mL (42%) |
| 4 Hours | Sediment: 1.4 mL (14%) | Sediment: 5.2 mL (52%) | Sediment: 5.4 mL (54%) | Sediment: 5.2 mL (52%) | Sediment: 3.8 mL (38%) | Sediment: 1.0 mL (10%) | Sediment: 1.0 mL (10%) |
| 6 Hours | Sediment: 1.4 mL (14%) | Sediment: 5.0 mL (50%) | Sediment: 5.4 mL (54%) | Sediment: 5.2 mL (52%) | Sediment: 4.0 mL (40%) | Sediment: 0.8 mL (8%) | Sediment: 0.8 mL (8%) |
| 1 Day | Sediment: 1.4 mL (14%) | Sediment: 5.0 mL (50%) | Sediment: 5.4 mL (54%) | Sediment: 5.2 mL (52%) | Sediment: 4.0 mL (40%) | Sediment: 0.8 mL (8%) | Sediment: 0.8 mL (8%) |
| 2 Days | Sediment: 1.4 mL (14%) | Sediment: 5.0 mL (50%) | Sediment: 5.4 mL (54%) | Sediment: 5.2 mL (52%) | Sediment: 3.8 mL (38%) | Sediment: 0.8 mL (8%) | Sediment: 0.8 mL (8%) |
| 5 Days | Sediment: 1.4 mL (14%) | Sediment: 5.0 mL (50%) | Sediment: 5.4 mL (54%) | Sediment: 5.2 mL (52%) | Sediment: 3.8 mL (38%) | Sediment: 0.8 mL (8%) | Sediment: 0.8 mL (8%) |
| 7 Days | Sediment: 1.4 mL (14%) | Sediment: 5.0 mL (50%) | Sediment: 5.4 mL (54%) | Sediment: 5.2 mL (52%) | Sediment: 3.8 mL (38%) | Sediment: 0.8 mL (8%) | Sediment: 0.8 mL (8%) |
| Degree of Flocculation | 3.5 | 12.5 | 13.5 | 13 | 9.5 | 2 | 2 |

Example 3

Compositions of 4% triamcinolone acetonide suspensions with 0.015% polysorbate 80 and different concentrations of CMC are described in Table 3.1 below. The mean volume particle size of the triamcinolone acetonide substance used in these compositions was 5-6 μm (measured using a Microtrac® S3000 instrument).

A settling study was carried out on these formulations by placing 10 mL samples of each of them in separate 10 mL graduated cylinders and recording sediment volume as a function of time. The results are provided in Table 3.2. The Degree of Flocculation in every case is >10. Thus, these compositions are representative examples of the highly flocculated compositions of the present invention.

TABLE 3.1:

Compositions of Triamcinolone Injection With CMC

| Composition | G | H | I | J |
|---|---|---|---|---|
| Triamcinolone | 4% | 4% | 4% | 4% |
| Polysorbate 80 | 0.015% | 0.015% | 0.015% | 0.015% |
| Carboxymethylcellulose sodium (7LFPH) | 0% | 0.25% | 0.5% | 0.75% |
| Sodium Chloride | 0.64% | 0.64% | 0.64% | 0.64% |
| Potassium Chloride | 0.075% | 0.075% | 0.075% | 0.075% |
| Calcium Chloride (Dihydrate) | 0.048% | 0.048% | 0.048% | 0.048% |
| Magnesium Chloride (Hexahydrate) | 0.03% | 0.03% | 0.03% | 0.03% |
| Sodium Acetate (Trihydrate) | 0.39% | 0.39% | 0.39% | 0.39% |
| Sodium Citrate (Dihydrate) | 0.17% | 0.17% | 0.17% | 0.17% |
| Sodium Hydroxide and/or Hydrochloric Acid | Adjust pH to 6.8 | Adjust pH to 6.8 | Adjust pH to 6.8 | Adjust pH to 6.8 |
| Water for Injection | qs to 100% | qs to 100% | qs to 100% | qs to 100% |

TABLE 3.2

Settling Study of Triamcinolone Acetonide Suspensions with 0.015% Polysorbate 80 at different CMC concentrations

| Time Point | Settling Phase in each 10 mL Volumetric Cylinder (Sedimentation Volume %) | | | |
|---|---|---|---|---|
| Composition | G | H | I | J |
| Polysorbate 80 Concentration | 0.015% | 0.015% | 0.015% | 0.015% |
| Carboxymethyl Cellulose Sodium, 7LFPH concentration | 0% | 0.25% | 0.5% | 0.75% |
| Initial (0 minutes) | Homogenous: 10 mL | Homogenous: 10 mL | Homogenous: 10 mL | Homogenous: 10 mL |
| 5 minutes | Sediment: 9.0 mL (90%) | Sediment: 9.8 mL (98%) | Sediment: 9.9 mL (99%) | Sediment: 0 |
| 10 minutes | Sediment: 8.2 mL (82%) | Sediment: 9.8 mL (98%) | Sediment: 9.6 mL (96%) | Sediment: 9.8 mL (98%) |
| 20 minutes | Sediment: 6.4 mL (64%) | Sediment: 9.0 mL (90%) | Sediment: 9.2 mL (92%) | Sediment: 9.6 mL (96%) |
| 30 minutes | Sediment: 6.4 mL (64%) | Sediment: 8.2 mL (82%) | Sediment: 9.0 mL (90%) | Sediment: 9.3 mL (93%) |
| 21 hours | Sediment: 4.8 mL (48%) | Sediment: 5.6 mL (56%) | Sediment: 5.2 mL (52%) | Sediment: 5.4 mL (54%) |
| 24 hours | Sediment: 4.8 mL (48%) | Sediment: 5.6 mL (56%) | Sediment: 5.4 mL (54%) | Sediment: 5.2 mL (52%) |
| Degree of Flocculation | 12 | 14 | 13.5 | 13 |

Example 4

A suspension composition representative of the compositions of this invention is described in Table 4.1 below. This formulation has 4% triamcinolone acetonide and 0.015% polysorbate 80. The viscosity of this formulation is about 5 cps. (Brookfield LVT viscometer using a CP-42 spindle at 60 rpm.)

The particle size measurement of a representative lot of this composition is provided in Table 4.2 (measurements were made using a Microtrac® S3000 instrument). The median particle size is 5.6 μm.

The force required to extrude this composition through a one-half inch 30 gauge needle attached to 1 mL tuberculin syringe is provided in Table 4.3. The results show that the required force was much smaller than that for Kenlaog-40 suspension (see Example 1, Table 1.3). In this case, there was no plugging of the 30 gauge needle.

A settling study of the type described in Example 2 was also performed and Composition K had a Degree of Flocculation of about 13, indicating it is a highly flocculated composition.

TABLE 4.1

Composition of Triamcinolone Acetonide Injection

| Component | Composition K | mg/mL |
|---|---|---|
| Triamcinolone Acetonide | 4.0 | 40 |
| Polysorbate 80 | 0.015 | 0.15 |
| Carboxymethylcellulose Sodium | 0.5 | 5.0 |
| Sodium Chloride | 0.55 | 5.5 |
| Potassium Chloride | 0.075 | 0.75 |
| Calcium Chloride (Dihydrate) | 0.048 | 0.48 |
| Magenesium Chloride (Hexahydrate) | 0.03 | 0.3 |
| Sodium Acetate (Trihydrate) | 0.39 | 3.9 |

TABLE 4.1-continued

Composition of Triamcinolone Acetonide Injection

| Component | Composition K | mg/mL |
|---|---|---|
| Sodium Citrate (Dihydrate) | 0.17 | 1.7 |
| Sodium Hydroxide and/or Hydrochloric Acid | Adjust pH to approx. 6.8 | Adjust pH to approx. 6.8 |
| Water for Injection | Qs to 100% | qs to 1 mL |

TABLE 4.2

Particle Size Data for a Representative Lot of
Triamcinolone Acetonide Suspension FID 110300

| Composition | Particle Size (μm) × $_{10}$ (by Microtrac) | Particle Size (μm) × $_{50}$ (by Microtrac) | Particle Size (μm) × $_{90}$ (by Microtrac) |
|---|---|---|---|
| K | 1.6 | 5.6 | 10.8 |

TABLE 4.3

Extrusion Force Data For Triamcinolone Acetonide Sterile Suspension
(1 mL Tuberculin Syringe with 30 GA × 1/2" needle)

| Composition | Average Load lbs force (Standard Deviation) | Maximum Load lbs force |
|---|---|---|
| K | 0.55 (0.205) | 1.1 (no plugging occurred) |

Example 5

Compositions of 1% and 8% tandospirone suspensions are provided in Table 5.1 below.

TABLE 5.1

Tandospione Suspension Compositions

| Component | Composition M | Composition N |
|---|---|---|
| Tandospirone | 1.0 | 80 |
| Polysorbate 80 or Tyloxapol | 0.005 | 0.02 |
| Carboxymethylcellulose Sodium | 0.5 | 0.5 |
| Sodium Chloride | 0.8 | 0.8 |
| Dibasic Sodium Phosphate Dodecahydrate | 0.25 | 0.25 |
| Sodium Hydroxide and/or Hydrochloric Acid | Qs to approx. 7.5 ± 0.2 | Qs to approx. 7.5 ± 0.2 |
| Water for Injection | Qs to 100% | Qs to 100% |

The invention claimed is:

1. A method of treating an ophthalmic disorder comprising administering by intravitreal injection an aqueous suspension composition, wherein the suspension composition does not contain a preservative, has a pH from 6-7.5, a viscosity from 2-12 cps, and a Degree of Flocculation of 9.5 or greater, and wherein the suspension composition consists essentially of:
   a) 4% (w/v) triamcinolone acetonide having a mean volume diameter of 3-10 μm;
   b) 0.5% (w/v) sodium carboxymethylcellulose;
   c) 0.002-0.015% (w/v) polysorbate 80;
   d) one or more pharmaceutically acceptable chloride salts selected from the group consisting of sodium chloride, potassium chloride, calcium chloride, and magnesium chloride as tonicity-adjusting agents in a total amount sufficient to cause the suspension composition to have an osmolality from 250-350 mOsm;
   e) water for injection;
   f) a buffering agent; and
   g) optionally a pH-adjusting agent.

2. A method of enhancing visualization of the vitreous during vitrectomy procedures comprising administering by intravitreal injection an aqueous suspension composition, wherein the suspension composition does not contain a preservative, has a pH from 6-7.5, a viscosity from 2-12 cps, and a Degree of Flocculation of 9.5 or greater, and wherein the suspension composition consists essentially of:
   a) 4% (w/v) triamcinolone acetonide having a mean volume diameter of 3-10 μm;
   b) 0.5% (w/v) sodium carboxymethylcellulose;
   c) 0.002-0.015% (w/v) polysorbate 80;
   d) one or more pharmaceutically acceptable chloride salts selected from the group consisting of sodium chloride, potassium chloride, calcium chloride, and magnesium chloride as tonicity-adjusting agents in a total amount sufficient to cause the suspension composition to have an osmolality from 250-350 mOsm;
   e) water for injection;
   f) a buffering agent; and
   g) optionally a pH-adjusting agent.

* * * * *